US 10,578,583 B2

(12) United States Patent
Dingman

(10) Patent No.: US 10,578,583 B2
(45) Date of Patent: Mar. 3, 2020

(54) SYSTEMS, APPARATUS, AND METHODS FOR INSPECTING SUBMERGED SURFACES

(71) Applicant: Delta SubSea, LLC, Montgomery, TX (US)

(72) Inventor: Scott Paul Dingman, Montgomery, TX (US)

(73) Assignee: Delta SubSea, LLC, Montgomery, TX (US)

(*) Notice: Subject to any disclaimer, the term of this patent is extended or adjusted under 35 U.S.C. 154(b) by 0 days.

(21) Appl. No.: 14/868,048

(22) Filed: Sep. 28, 2015

(65) Prior Publication Data
US 2016/0231281 A1  Aug. 11, 2016

Related U.S. Application Data

(60) Provisional application No. 62/114,314, filed on Feb. 10, 2015, provisional application No. 62/056,305, filed on Sep. 26, 2014.

(51) Int. Cl.
G01N 27/90 (2006.01)
G01B 7/06 (2006.01)
B63G 8/00 (2006.01)
B63C 11/52 (2006.01)
G01B 17/02 (2006.01)
F16L 101/30 (2006.01)

(52) U.S. Cl.
CPC .............. *G01N 27/90* (2013.01); *B63C 11/52* (2013.01); *B63G 8/001* (2013.01); *G01B 7/06* (2013.01); *G01B 7/10* (2013.01); *G01B 17/02* (2013.01); *B63G 2008/002* (2013.01); *B63G 2008/005* (2013.01); *F16L 2101/30* (2013.01); *G01N 27/902* (2013.01)

(58) Field of Classification Search
CPC combination set(s) only.
See application file for complete search history.

(56) References Cited

U.S. PATENT DOCUMENTS

| 4,929,896 A | * | 5/1990 | Lara | G01B 7/06 324/229 |
| 4,995,320 A | * | 2/1991 | Sato | B61B 13/04 104/118 |

(Continued)

OTHER PUBLICATIONS

E Slomp et al., SUBSEA PEC: The NDT Diverless Robotic System for the Pipeline Coorosion Inspection, SPE 161662, Nov. 11, 2012, pp. 1-21.

Primary Examiner — Minh Q Phan
(74) Attorney, Agent, or Firm — Jason P. Mueller; Adams and Reese LLP

(57) ABSTRACT

Embodiments of the present invention include systems, apparatuses, and methods that include a pipeline inspection apparatus containing a carriage, a first member including at least a first and second sensor configured to take a first round of measurements of a pipe, a second member including at least a third and fourth sensor configured to take a first round of measurements of the pipe, and a multiplexer. The first and second members are attached to opposite side members of the carriage. The carriage, first member, and second member are configured to surround a section of the pipe and are movably mountable on the pipe. The multiplexer receives a signal from the at least first, second, third, and fourth sensors and creates a measurement signal.

31 Claims, 5 Drawing Sheets

(56) References Cited

U.S. PATENT DOCUMENTS

| | | | |
|---|---|---|---|
| 5,698,854 A * | 12/1997 | Gupta | G01N 23/18 250/358.1 |
| 2002/0129641 A1 | 9/2002 | Tucker et al. | |
| 2004/0245997 A1 | 12/2004 | Plotnikov et al. | |
| 2011/0163740 A1 | 7/2011 | Russell et al. | |

* cited by examiner

SYSTEMS, APPARATUS, AND METHODS FOR INSPECTING SUBMERGED SURFACES

CROSS-REFERENCE TO RELATED APPLICATIONS

This application claims benefit of U.S. Provisional Application No. 62/056,305, filed Sep. 26, 2014, and U.S. Provisional Application No. 62/114,314, filed Feb. 10, 2015, which are incorporated herein by reference.

FIELD

The present invention relates generally to non-destructive testing systems, apparatuses, and methods, and in particular though non-limiting embodiments, to systems, apparatuses and methods for inspecting submerged pipelines.

BACKGROUND

A submerged or submarine pipeline is a pipeline passing under water, which is typically laid on the seabed, or inside a trench below the seabed. The pipeline may also be partially located on-land. Submarine pipelines are used primarily to carry oil or gas but may also be used to transport other materials.

Submerged pipelines are often wrapped with insulating materials. Insulating materials provide many benefits. For example, insulating materials may provide flow assurance by maintaining flow rates. This, in turn, optimizes productivity and lowers processing costs. Also, insulating subsea equipment and piping reduces the costs of cooling reservoir fluids and helps maintain temperatures so that waxes and hydrates do not form, thereby minimizing the risk of diminished flow rates and blockages.

Despite various prevention efforts, pipelines are susceptible to corrosion, which causes costly damage every year. As a result of this corrosion, pipeline sections often have to be taken out of service and replaced. In order to identify pipeline areas or sections in need of repair or replacement, inspection of the pipelines is generally required. Detection of areas of corrosion can allow for corrective actions prior to a potentially catastrophic event. Various techniques may be employed to detect corrosion in pipelines.

Inspection of submerged pipelines, including pipelines at depths of 4,000 meters, poses additional difficulties over inspections of pipeline above water or in relatively shallow water. Certain inspection techniques, such as infrared inspections, require direct contact with the pipeline. To utilize such techniques on submerged pipelines, any insulating material as well as any other marine build up on the pipes must be removed before testing. Preparation for testing can be very expensive. Other techniques provide for external inspection of pipelines without removing the insulating material and/or marine buildup. For example, pulsed eddy current (PEC) sensors, such as the Applus RTD® INCOTEST, may be utilized to survey ferrous pipes and vessels through thermal insulation, protective coatings and marine buildup. PEC sensors are typically deployed as a single sensor by a diver or remotely operated vehicle (ROV). Manipulation of the sensor along pipelines, particularly deeply submerged pipelines, can be difficult, time-consuming, and inefficient.

Accordingly, a need exists for improved apparatuses and methods to more efficiently inspect submerged surfaces, including submerged pipelines.

SUMMARY

Embodiments of the present invention provide for improved systems, apparatuses and methods for inspecting submerged surfaces. An exemplary embodiment provides for apparatuses, systems, and methods for the quick and efficient inspection of submerged pipelines using an ROV and an inspection apparatus containing multiple PEC sensors. The PEC sensors may be configured to take measurements of a section of the pipeline on which the inspection apparatus is placed and send multiple signals which are eventually converted into a single measurement signal for conveyance to software which may be on the ROV. The software calculates an average wall thickness of the section of the pipeline from this measurement signal. In an exemplary embodiment, a second measurement of this section of pipe may be taken using an ultrasonic sensor if the average wall thickness of the section of pipe is below a desired amount.

An exemplary embodiment of the present invention provides for an inspection apparatus, system, and method that may be employed for ROV deepwater inspection of non-piggable pipelines. The present invention is based on the PEC principle and presents a reliable method to survey ferrous pipes and vessels through their thermal insulation, marine build-up, and protective coatings. The PEC sensors may be utilized to identify areas on the pipelines in need of further inspection. If such a need is detected, additional inspection methods such as ultrasonic inspection may then be utilized.

The PEC based testing with PEC sensors disclosed in the present invention provides for the detection of surface and subsurface corrosion of pipelines. The PEC sensors do not need to contact the underlying pipe for measurements, preventing the need for removal of marine buildup or protective/insulating layers, which provides substantial savings in time and costs associated with other inspection approaches. PEC sensors can perform in temperatures ranging from approximately −150° C. to approximately 500° C. PEC sensors have a measurement accuracy of approximately +/−5%. PEC based measurements and testing with PEC sensors may be efficiently performed in-line at depths of approximately 4,000 meters. Components may be evaluated at variable depths, which may be achieved through measurement at a range of frequencies or through different coil sizing within the PEC sensors. Testing with PEC sensors does not require any consumable chemicals and allows for up to 1,000 measurements per day, with the duration of each measurement lasting approximately four to approximately ten seconds. The PEC sensors may be operated on mains power or batteries.

In an example embodiment of the present disclosure, a pipeline inspection apparatus is provided. The apparatus includes a carriage, a first member including at least a first and second sensor configured to take a first round of measurements of a pipe, a second member including at least a third and fourth sensor configured to take a first round of measurements of the pipe, and a multiplexer. The first and second members may be attached to opposite side members of the carriage. The carriage, first member, and second member may be configured to surround a section of the pipe and be movably mountable on the pipe. The multiplexer may receive a signal from at least the first, second, third, and fourth sensors and create a measurement signal. The at least first, second, third, and fourth sensors may be pulsed eddy current (PEC) sensors. The apparatus may include at least one roller attached to each opposing end of the carriage, first member, and second member, the roller configured to assist in moving the inspection apparatus along the pipeline. The apparatus may include an attachment configured to attach to an ROV. The multiplexer may be configured to convey the measurement signal to software on the ROV. The apparatus may include a first extension arm connected to the first member and the carriage, the first extension arm configured to rotate the first member relative to the carriage. The apparatus may also include a second extension arm connected to the second side member and the carriage, the second extension arm configured to rotate the second member relative to the carriage. The first and second extension arms may be hydraulic cylinders.

The apparatus may include a handle mounted on the carriage, the handle configured to provide for manual or ROV-assisted manipulation and placement of the apparatus. Each measurement of the first round of measurements of the at least first, second, third, and fourth sensors may be six inches. The first round of measurements may include twelve measurements. The first round of measurements may take fifteen seconds.

In an example embodiment of the present disclosure, a method for inspecting pipelines is provided. The method includes placing an inspection apparatus upon a pipeline. The apparatus includes a carriage, a first member including at least a first and second sensor configured to take a first round of measurements of a pipe, a second member including at least a third and fourth sensor configured to take a first round of measurements of the pipe, and a multiplexer. The first and second members may be attached to opposite side members of the carriage. The carriage, first member, and second member may be configured to surround a section of the pipe and be movably mountable on the pipe. The multiplexer may receive a signal from the at least first, second, third, and fourth sensors and create a measurement signal. The method includes connecting an attachment of the inspection apparatus to an ROV, rotating the carriage, first member, and second member relative to each other such that the inspection apparatus fits on the pipeline, taking measurements of the pipe using the at least first, second, third, and fourth sensors to create signals from each of the at least first, second, third, and fourth sensors, sending the signals from each of the at least first, second, third, and fourth sensors to the multiplexer for conversion to the measurement signal, conveying the measurement signal from the multiplexer to software on the ROV, and moving the inspection apparatus along the submerged pipeline using the ROV after each round of the measurements. The first, second, third, and fourth sensors may be pulsed eddy current (PEC) sensors.

The method may include using at least one roller attached to each opposing end of the carriage, first member, and second member, the roller configured to assist in moving the inspection apparatus along the pipeline. The method may include connecting a first extension arm to the first member and the carriage, the first extension arm configured to rotate the first member relative to the carriage. The method may further include connecting a second extension arm to the second side member and the carriage, the second extension arm configured to rotate the second member relative to the carriage. The first and second extension arms may be hydraulic cylinders. The method may include connecting at least one hydraulic line between the ROV and the apparatus, the at least one hydraulic line configured to extend and retract the hydraulic cylinders. The method may include connecting at least one electrical line between the ROV and the apparatus, the at least one electrical line configured to provide power to run the inspection apparatus. The apparatus may have a total of approximately four to approximately thirty-two PEC sensors. Each of the first and second members may have at least two and at most sixteen PEC sensors.

The method may include using the software to calculate an average wall thickness of the section of the pipe from the measurement signal. The method may include taking a second round of measurements of the section of pipe if the average wall thickness of the section of pipe is below a desired amount, where the second measurement is taken using a fifth sensor. The fifth sensor may be an ultrasonic sensor. The method may include taking a new round of measurements after moving the apparatus three inches down the pipe. The method may include taking a new round of measurements after moving the apparatus five feet down the pipe. The first and fourth sensors, second and fourth sensors, and first and third sensors may alternate in taking rounds of measurements of the pipe to avoid magnetic interference.

In an example embodiment of the present disclosure, a system for inspecting a submerged pipe is provided. The system includes a remotely operated vehicle (ROV) and an inspection apparatus attached to the ROV. The apparatus includes a carriage, a first member including at least a first and second sensor configured to take a first round of measurements of a pipe, a second member including at least a third and fourth sensor configured to take a first round of measurements of the pipe, and a multiplexer. The first and second members may be attached to opposite side members of the carriage. The carriage, first member, and second member may be configured to surround a section of the pipe and be movably mountable on the pipe. The multiplexer may receive a signal from the at least first, second, third, and fourth sensors and create a measurement signal. The measurement signal may be conveyed by the multiplexer to software on the ROV and analyzed to determine an average wall thickness of the section of pipe measured by the inspection apparatus. The at least first, second, third, and fourth sensors may be pulsed eddy current (PEC) sensors. The system may include a first extension arm connected to the first member and the carriage, the first extension arm configured to rotate the first member relative to the carriage. The system may further include a second extension arm connected to the second side member and the carriage, the second extension arm configured to rotate the second member relative to the carriage. The first and second extension arms may be hydraulic cylinders.

DETAILED DESCRIPTION

Figure 1:
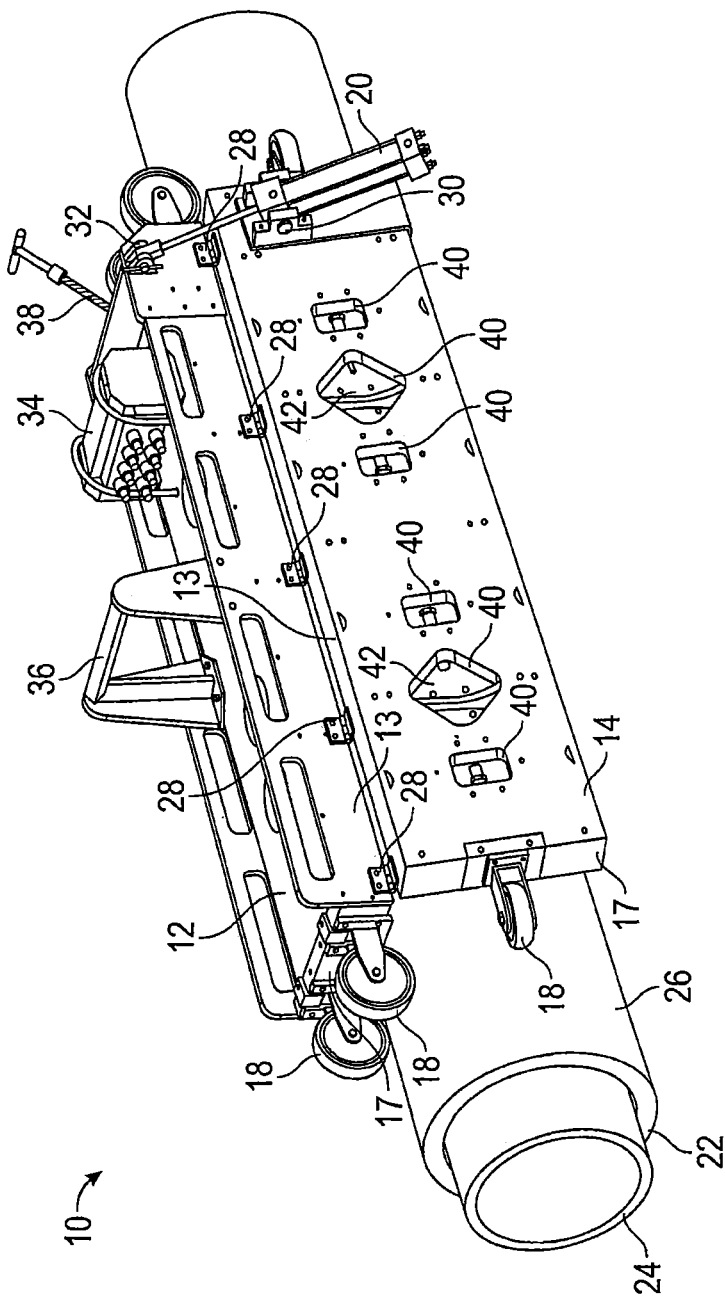
FIG. 1 is an isometric view of an inspection apparatus positioned on a section of insulated pipe, according to an exemplary embodiment of the present invention.

The present disclosure provides apparatuses, systems, and methods for the inspection of submerged surfaces. An exemplary embodiment provides apparatuses, systems, and methods for the inspection of submerged pipelines. Embodiments include an inspection apparatus having a plurality of PEC sensors disposed therein. The inspection apparatus may be configured for attachment to an ROV. The inspection apparatus may have a plurality of members or plates, each member/plate containing at least two PEC sensors. The members or plates may be attached to opposite side members of a carriage. The carriage and members/plates may be configured to surround a section of a pipe and may be movably mountable on the pipe. Each PEC sensor may take a measurement of a section of pipe and send at least one signal. An embodiment of the present invention may provide for an inspection apparatus having a single superstructure including a plurality of PEC sensors. The inspection apparatus may be configured to wrap around pipelines of various diameters. The inspection apparatus may include mechanical connections between members or plates such that the members or plates can be closed and/or opened around a pipe. The plurality of PEC sensors may be connected to a multiplexer that receives the at least one signal from each sensor and combine the at least one signal from each sensor into a measurement signal. The multiplexer may convey this measurement signal to software which may be on the ROV, to determine a wall thickness of a section of the pipeline. The inspection apparatus may include a battery or may alternatively be run using main power from the ROV.

According to exemplary embodiments of the present invention, methods are provided for inspecting pipelines. According to an exemplary embodiment, a method includes placing an inspection apparatus as disclosed herein upon a pipeline such that the apparatus securely fits on the pipeline, and then connecting the apparatus to an ROV. A sensor within the apparatus may then be used to take multiple measurements of a section of the pipeline and create at least one signal based on each measurement. The signals from each measurement may then be combined into a single measurement signal and sent to the ROV. An average wall thickness of the section of the pipeline may then be calculated from this measurement signal. If desired, a second measurement of this section of pipe may be taken using a second sensor if the average wall thickness of the section of pipe is below a specific amount. The inspection apparatus may be moved along the submerged pipeline using the ROV after each round of the measurements.

Employing multiple PEC sensors allows for taking measurements on multiple points along the pipe simultaneously, which substantially increases the amount of pipeline that may be inspected within a given period of time. The present invention may allow for miles of pipeline to be inspected in a single day using this configuration of PEC sensors. The inspection apparatus may be securely and quickly guided along the pipeline using the connection to the ROV. The inspection apparatus may be employed to inspect vast sections of pipeline for potential problem areas. Any potential problem areas may then be subjected to additional testing, such as ultrasonic testing, which is substantially slower (couple of feet per day). In this way, the present invention allows for efficient, low cost inspection of pipeline, while identifying areas of pipeline that may warrant further inspection from less efficient methods, vastly increasing overall efficiency. Although discussed herein in conjunction with pipelines, PEC testing may be performed on vessels or other surfaces. Embodiments of the present invention allow for quick inspection of pipelines without removing insulation on the pipelines; if a problem area is detected, then the insulation may be removed and the pipeline may be further inspected using another inspection device.

Figure 2:
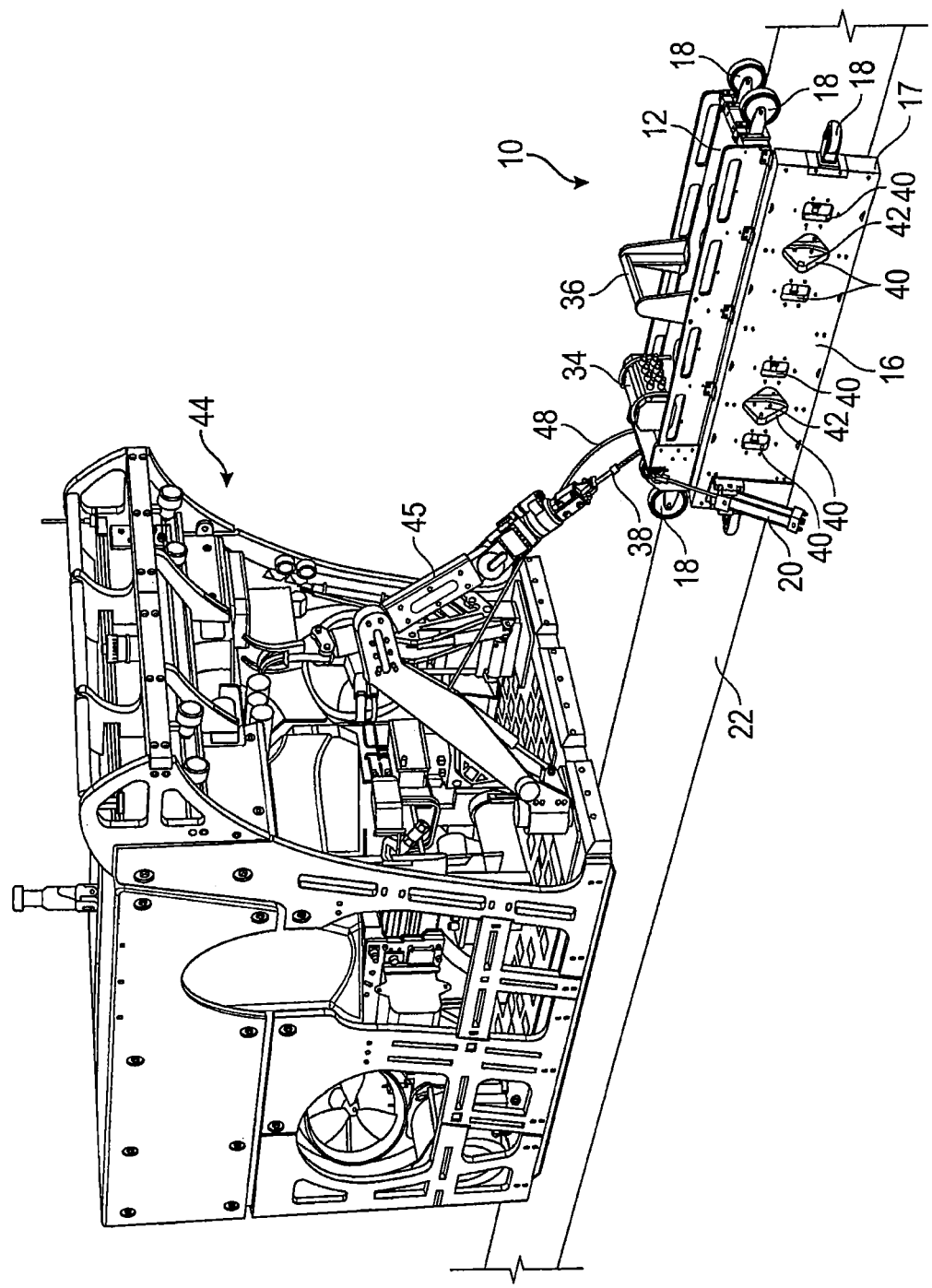
FIG. 2 is an isometric view of the inspection apparatus shown in FIG. 1 connected to an ROV, according to an exemplary embodiment of the present invention.
Figure 3:
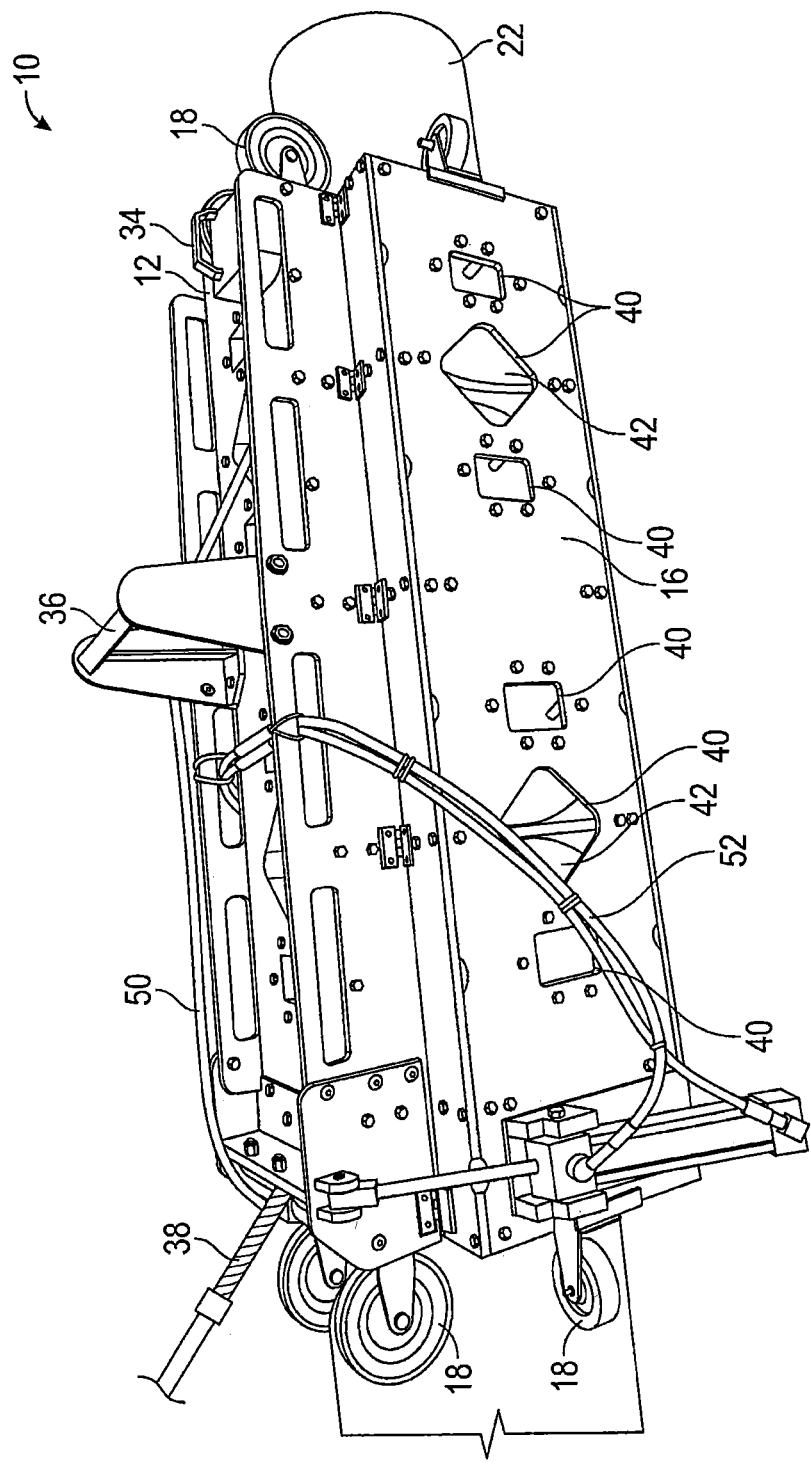
FIG. 3 is a side view of an inspection apparatus positioned on a section of insulated pipe, according to an exemplary embodiment of the present invention.
Figure 4:
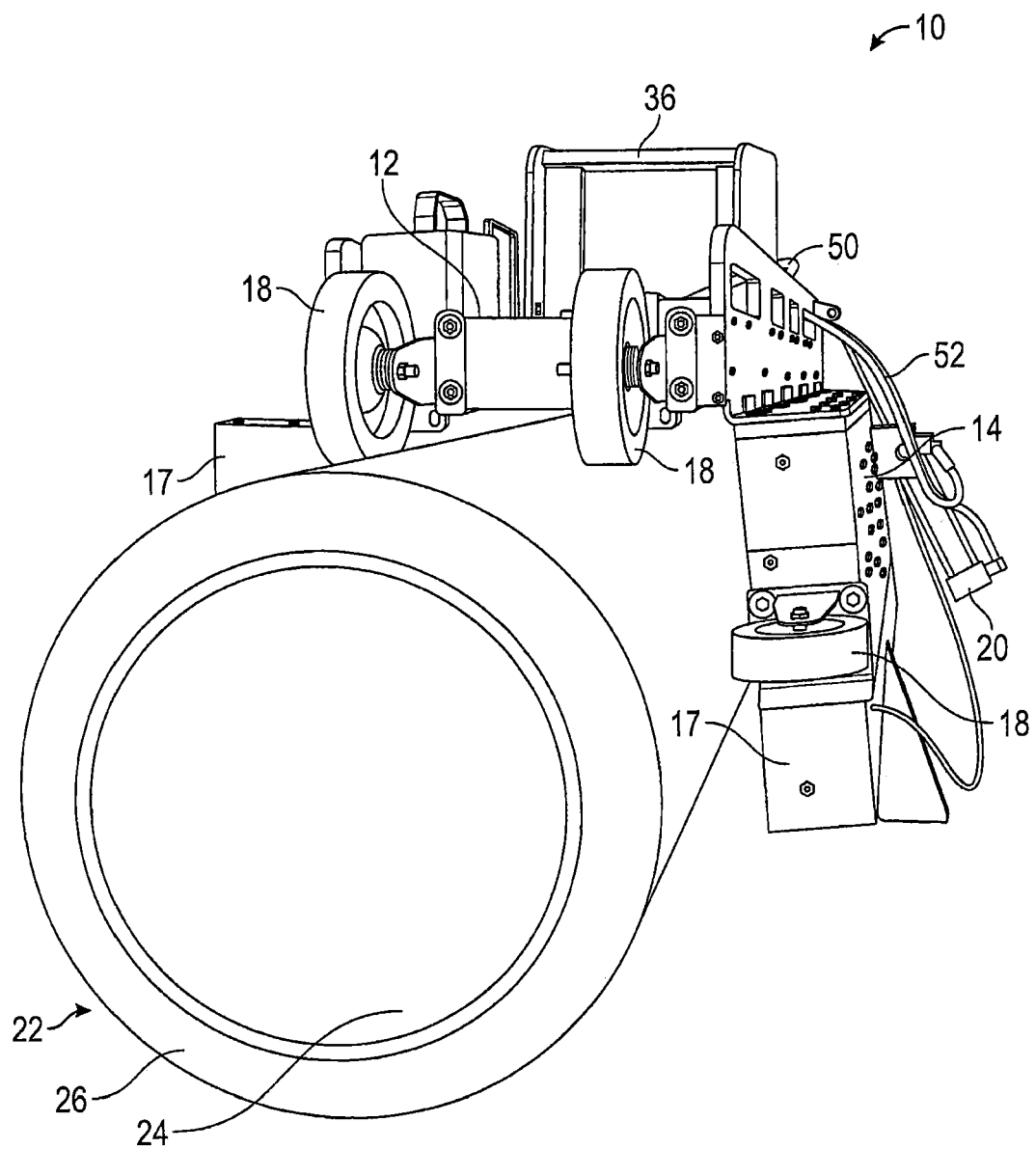
FIG. 4 is an end view of the inspection apparatus shown in FIG. 3.

Referring to FIGS. 1 to 4, various embodiments and views of components of an inspection apparatus 10 are shown. FIG. 1 shows an exemplary embodiment of an inspection apparatus 10 positioned on a section of insulated pipe 22. FIG. 2 shows the same inspection apparatus 10 from FIG. 1 connected to an ROV 44. FIGS. 3 and 4 show side and end views, respectively, of an embodiment of the inspection apparatus 10. Referring now to FIGS. 1 to 4, an inspection apparatus 10 is shown positioned upon an insulated pipe 22 having an inner ferrous layer 24 and an outer insulation layer 26. Inspection apparatus 10 has a plurality of members or plates 14, 16 and a carriage or center plate 12. Each of the plurality of members or plates 14, 16 and carriage or center plate 12 has a pair of opposing side edges 13 and a pair of opposing short edges 17. The plurality of members/plates 14, 16 and carriage/center plate 12 may be hinged together along at least one of the opposing side edges 13 of each of the plurality of members/plates 14, 16 and carriage/center plate 12. In an exemplary embodiment, the inspection apparatus 10 has a center plate or carriage 12, first member or side plate 14, and second member or side plate 16. First and second members/side plates 14, 16 are attached to the center plate/carriage 12 using a plurality of hinges 28 along their respective side edges 13 such that the first and second side members/plates 14, 16 may be rotated relative to center plate/carriage 12. Although the present invention discloses the use of hinges 28, other mechanical means may be used to attach the first and second members or side plates 14, 16 to the center plate or carriage 12, including circumferential straps, bolts, magnets, ties, quick releases, snap locks, or any combination thereof and/or any other suitable means.

Rotation of members/side plates 14, 16 may be provided by an extension arm 20 having a connection 32 with center plate/carriage 12 and a connection 30 with members/side plates 14, 16. Each member or side plate 14, 16 may be provided with the extension arm 20. In exemplary embodiments, apparatus 10 includes a first extension arm 20 connected to each of the first member or side plate 14 and the center plate or carriage 12, and a second extension arm 20 connected to each of the second member or side plate 16 and the center plate or carriage 12. First extension arm 20 is configured to rotate the first member or side plate 14 relative to the center plate or carriage 12. Second extension arm 20 is configured to rotate the second member or side plate 16 relative to the center plate or carriage 12. The plurality of members/plates 14, 16 and carriage/center plate 12 may be rotated to fit around the pipe 22 using the first and second extension arms 20.

Extension arms 20 may be hydraulic cylinders and may have hydraulic lines 52 connected thereto. See FIG. 3. Hydraulic lines 52 may be used to extend and retract the extension arms 20. Hydraulic lines 52 may be controlled via connections to the ROV 44. ROV 44 may thus control opening and closing of inspection apparatus 10 around pipe 22. As shown in FIGS. 3 and 4, an electrical line 50 may also be connected between the ROV 44 and inspection apparatus 10, the electrical line 50 configured to provide power to run the inspection apparatus (and enclosed sensors).

Each of the plurality of members/plates 14, 16 has a plurality of plate apertures 40 through which water may pass into the interior spaces of each of the plurality of members/plates 14, 16. Sensors 42 are contained in the interior spaces of each of the plurality of members or plates 14, 16. In exemplary embodiments, sensors are PEC sensors 42. In alternative embodiments, carriage/center plate 12 may also include apertures 40 and/or PEC sensors 42 contained within its interior spaces. Placement of inspection apparatus 10 around pipe 22 allows for an arrangement of a plurality of PEC sensors 42 over pipe 22 simultaneously, thereby allowing multiple points along the pipe 22 to be inspected simultaneously, which substantially increases the amount of pipeline 22 that may be inspected within a given period of time. Although PEC sensors are discussed herein, other types of sensors including ultrasonic sensors may also be used in alternative embodiments of the invention, either in a separate apparatus or the same apparatus.

In the embodiments shown in FIGS. 1 to 4, each member or side plate 14, 16 has four PEC sensors 42 contained therein. As shown, the configuration provides for a total of eight PEC sensors 42 in inspection apparatus 10. Alternative embodiments may contain more or less PEC sensors 42 within each of the plurality of members or plates 14, 16, carriage 12, and/or any other members or plates employed to house the PEC sensors 42. Each of the plurality of members or plates 14, 16 may have at least two and at most sixteen PEC sensors 42. In certain embodiments, thirty-two PEC sensors 42 in total may be provided within the inspection apparatus 10.

Each of the plurality of PEC sensors 42 may be connected to multiplexer 34 such that each of the plurality of PEC sensors 42 may take a measurement of a section of pipe 22 and send a separate signal to multiplexer 34. Multiplexer 34 may be mounted on any location on the carriage/center plate 12. See, e.g., FIGS. 1 and 3. As shown in FIG. 2, multiplexer 34 has a single cable 48 connecting multiplexer to ROV 44. Multiplexer 34 may be configured to receive the signal from each PEC sensor 42 and combine the signal into a single measurement signal. Multiplexer 34 may also be configured to convey the measurement signal to the ROV 44. Arm 45 of ROV 44 may be connected to inspection apparatus 10 via ROV connector 38, which may allow ROV 44 to move inspection apparatus 10 along pipe 22. Inspection apparatus 10 may also include a handle 36 mounted on the center plate/carriage 12. Handle 36 may be configured to provide for manipulation and placement of inspection apparatus 10 via arm 45 of ROV 44 or manual manipulation.

Rollers 18 may be attached to the plurality of members or plates 14, 16 and carriage or center plate 12 at opposing short edges 17. In exemplary embodiments, two rollers 18 are attached at each short edge 17 of center plate or carriage 12 and one roller 18 is attached at each short edge 17 of members or side plates 14, 16. Rollers 18 are configured to assist in placement and movement of apparatus 10 along pipe 22.

Figure 5:
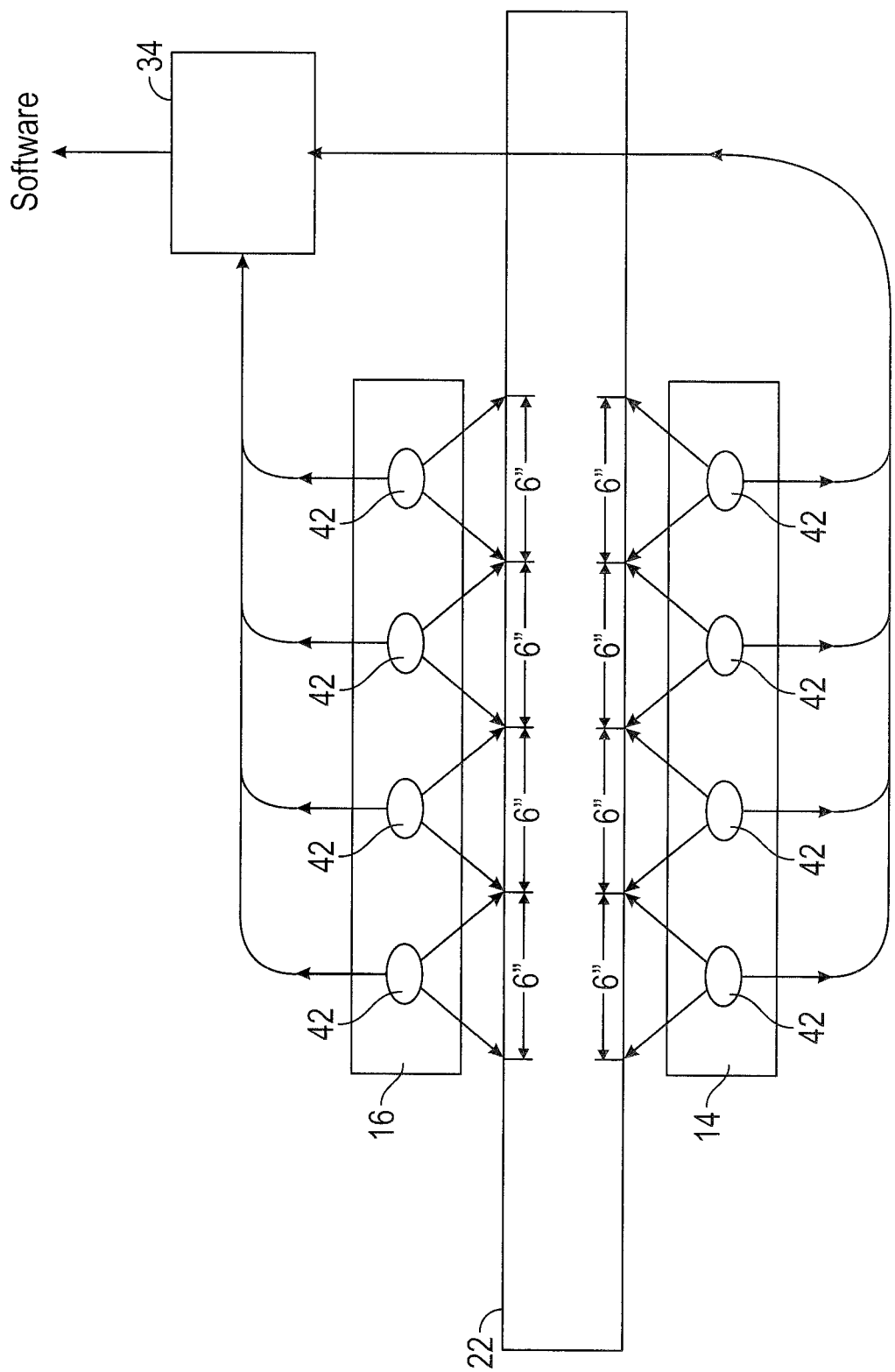
FIG. 5 is a schematic diagram of a system for inspecting pipelines, according to an exemplary embodiment of the present invention.

Referring now to FIG. 5, a schematic diagram of a system for inspecting pipelines is shown. In an exemplary embodiment, four PEC sensors 42 are placed within each member/plate 14, 16. Each PEC sensor 42 may be separated by a space, with the sensors 42 and the space between them correlating to an area of the pipeline 22. Sensors 42 may follow a specific pattern in taking measurements of the pipe 22. Apparatus 10 may be configured so that each sensor 42 takes readings of the pipe 22 on alternate, not adjacent, probes to minimize and/or avoid any possible interferences of the magnetic fields when taking measurements. For example, in the four-sensor configuration shown in FIG. 5, the first and fourth sensor will take simultaneous measurements, the second and fourth sensor will take simultaneous measurements, and the first and third sensor will take simultaneous measurements. However, the first and second sensor, the second and third sensor, and the third and fourth sensor, will not take simultaneous measurements of the pipe.

Each of the plurality of PEC sensors 42 may then take measurements for its footprint and send the measurements to a multiplexer 34. The footprint is the area of the pipe 22 measured by the sensors 42. In an exemplary embodiment, the footprint of each PEC sensor 42 on the pipe 22 is six inches. So, in the embodiment shown with four sensors, the total footprint covered by the measurements is twenty-four inches, or two feet. In exemplary embodiments, each PEC sensor 42 will take one round of twelve measurements in fifteen seconds. Although shown in the four-sensor configuration described above, each member/plate 14, 16 may have two to sixteen sensors 42, thereby increasing the total footprint covered, as well as increasing the options for similarly alternating sensor 42 measurements and making duplicate measurements. Further, although shown as PEC sensors 42, other type of sensors may be used to take these measurements. If other non-PEC sensors are used, apparatus 10 and non-PEC sensors may have to be brought into contact with surface of the pipeline 22 to perform measurements.

Once the PEC sensors 42 take a round of measurements, the apparatus 10 may then be moved along a desired distance and direction of the pipe 22. In exemplary embodiments, apparatus 10 is moved three inches along the pipe 22. Once the apparatus 10 is moved along the desired distance and direction of the pipe 22, a new round of measurements of the pipe 22 may be taken with the PEC sensors 42 such that an overlap of a section of the pipe may be measured. For example, in the embodiment shown in FIG. 5 with four sensors 42 in each member 14, 16, the second round of measurements will contain an overlap of twenty-one inches of the pipe 22 once apparatus 10 is moved three inches.

Each measurement taken by the PEC sensors 42 may then be collectively sent via cables to the multiplexer 34. In exemplary embodiments, multiplexer 34 receives and combines the signals from each measurement into a single measurement signal, and conveys this measurement signal to software located on the ROV 44. In an alternative embodiment, the multiplexer 34 may send the signal to an external line, the external line connected to software located on an exterior platform such as a topside ship. The signal may then be processed to calculate wall thickness using the method disclosed in U.S. Pat. Nos. 4,843,320 and 4,843,319, both of which are incorporated herein by reference. Particularly, the patents disclose using transient electromagnetic probing (TEMP), which allows for the remote probing of a section of pipeline by inducing a current into the pipeline, analyzing a decay of the current, and comparing the decay to that of a pipeline free of irregularities to thereby determine thickness of the section of pipeline. Various measurements of thickness from each of the sensors 42 may be averaged to provide an average thickness of an area of the submerged pipeline 22. In an exemplary embodiment, the software on the ROV 44 or on a topside platform measures and detects the difference between a known/standard pipeline thickness and the thickness of the pipe 22 being inspected to calculate a percentage of the thickness of the pipe 22 remaining after corrosion. This percentage may be used to determine whether the thickness of the pipe 22 is below a specific/desired amount and therefore requires further inspection. In exemplary embodiments, the pipeline 22 has a wall thickness in the range of approximately 6 mm to approximately 65 mm, and a diameter of approximately 50 mm. In an exemplary embodiment, the pipeline is a low-alloyed carbon steel pipeline 22. Pipeline 22 may be laminated and if so, the thickness of the pipeline 22 without lamination may be measured. Pipeline 22 may have an insulation thickness of up to 200 mm. One advantage of the present invention is the ability to take quick measurements through insulation on a pipeline or other submerged surface to determine problem areas. If a problem area is detected, the insulation may be removed and further inspection may be performed. This preliminary type of inspection therefore allows for fast inspection of large spans of pipeline or submerged surface.

According to exemplary embodiments of the present invention, methods are provided for inspecting pipelines/surfaces. In exemplary embodiments, a method includes placing the inspection apparatus 10 as described herein upon a submerged pipeline 22 such that the apparatus 10 securely fits on the pipeline 22. ROV 44 may then be attached to the apparatus 10 by connecting an ROV attachment 38 to arm 45 of ROV 44, allowing ROV 44 to move inspection apparatus 10 along pipe 22. Sensors 42 within apparatus 10 may then be used to take a first round of measurements of a section of the submerged pipeline 22, create signals based on each measurement, and send the signals from each measurement to a multiplexer 34. In an exemplary embodiment, sensor is a PEC sensor 42. Multiplexer 34 may then receive the signals from each first measurement, combine them into a single measurement signal, and convey this measurement signal to software which may be on the ROV 44 or on a topside platform. If the average wall thickness of the section of pipe 22 is below a specific amount, i.e. prone to failure, a second round of measurements of this section of pipe 22 may be taken using a second sensor. In an exemplary embodiment, the second sensor is an ultrasonic sensor. Once the section of pipe 22 is measured, the ROV 44 may advance the apparatus 10 further along a desired direction of the pipe 22 to take a second round of measurements until the inspection is completed. In exemplary embodiments, ROV 44 may advance apparatus 10 five feet along pipe 22 to take the second round of measurements. The first and second measurements may be taken in temperatures ranging from approximately −150° C. to approximately 500° C. Sensors 42 may have a measurement accuracy of approximately +/−5%.

While the embodiments are described with reference to various implementations and exploitations, it will be understood that these embodiments are illustrative and that the scope of the inventions is not limited to them. Many variations, modifications, additions, and improvements are possible. Further still, any steps described herein may be carried out in any desired order, and any desired steps may be added or deleted.

What is claimed is:

1. An inspection apparatus, comprising:
   a carriage;
   a first member having a first group of sensors including at least a first sensor and a second sensor configured to take a first round of measurements of a pipe, the first member attached to a first side of the carriage;
   a second member having a second group of sensors including at least a third sensor and a fourth sensor configured to take a second round of measurements of the pipe, the second member attached to a second side of the carriage opposite the first side; and
   a multiplexer device that receives at least one respective signal from at least one of the first sensor, the second sensor, the third sensor, or the fourth sensor, wherein the multiplexer device generates a measurement signal using at least the at least one respective signal;
   wherein all adjacent sensors alternate in taking rounds of measurements of the pipe to avoid magnetic interference; and
   wherein the carriage, the first member, and the second member are configured to surround a portion of a section of the pipe and are movably mountable on the pipe.

2. The inspection apparatus of claim 1, wherein the at least first sensor, second sensor, third sensor, and fourth sensors comprise respective pulsed eddy current (PEC) sensors.

3. The inspection apparatus of claim 1, further comprising at least one roller attached to each opposing end of the carriage, first member, and second member, the at least one roller configured to assist in placing and moving the inspection apparatus along the pipe.

4. The inspection apparatus of claim 1, further comprising an attachment member configured to attach to a remotely operated vehicle (ROV).

5. The inspection apparatus of claim 4, wherein the multiplexer device is configured to send the measurement signal to a software component on the ROV.

6. The inspection apparatus of claim 1, further comprising:
   a first extension arm connected to the first member and the carriage, the first extension arm configured to rotate the first member relative to the carriage, and
   a second extension arm connected to the second side member and the carriage, the second extension arm configured to rotate the second member relative to the carriage.

7. The inspection apparatus of claim 6, wherein the first extension arm and the second extension arm comprise respective hydraulic cylinders.

8. The inspection apparatus of claim 1, further comprising a handle mounted on the carriage, the handle configured to provide for manual or ROV-assisted manipulation and placement of the apparatus.

9. The inspection apparatus of claim 1, wherein each measurement of the first round of measurements of the at least first sensor and second sensor is associated with a first six-inch portion of the pipe, and wherein the at least third sensor and fourth sensor is associated with a second six-inch portion of the pipe.

10. The inspection apparatus of claim 1, wherein the first round of measurements includes twelve measurements, and wherein the second round of measurements includes twelve measurements.

11. The inspection apparatus of claim 1, wherein the first round of measurements spans about 15 seconds, and wherein the second round of measurements spans about 15 seconds.

12. A method of inspecting pipelines, comprising:
    placing an inspection apparatus upon a pipeline, wherein the inspection apparatus comprises:
    a carriage;
    a first member having a first group of sensors including at least a first sensor and a second sensor configured to take a first round of measurements of a section of a submerged pipeline, the first member attached to a first side of the carriage;
    a second member having a second group of sensors including at least a third sensor and a fourth sensor configured to take a second round of measurements of the section of the submerged pipeline, the second member attached to a second side of the carriage opposite the first side; and
    a multiplexer device that receives a respective signal from each one of the first sensor, the second sensor, the third sensor, and the fourth sensor, wherein the multiplexer device generates a measurement signal using at least the respective signal from each one of the first sensor, the second sensor, the third sensor, and the fourth sensor;

wherein all adjacent sensors alternate in taking rounds of measurements of the submerged pipeline to avoid magnetic interference and wherein the carriage, the first member, and the second member are configured to surround the section of the submerged pipeline and are movably mountable on the submerged pipeline, connecting an attachment of the inspection apparatus to a remotely operated vehicle (ROV);

rotating the carriage, the first member, and the second member relative to each other such that the inspection apparatus fits on the submerged pipeline;

taking measurements of the submerged pipeline using the at least first sensor, the second sensor, the third sensor, and the fourth sensor to create signals from each of the at least first sensor, second sensor, third sensor, and fourth sensor;

sending the signals from each of the at least first sensor, second sensor, third sensor, and fourth sensor to the multiplexer for conversion to the measurement signal;

sending the measurement signal from the multiplexer device to a software component on the ROV;

moving the inspection apparatus along the pipeline using the ROV after each one of the first round of measurements and the second round of measurements.

13. The method of claim 12, wherein the at least first sensor, second sensor, third sensor, and fourth sensor comprise respective pulsed eddy current (PEC) sensors.

14. The method of claim 12, further comprising using at least one roller attached to each opposing end of the carriage, first member, and second member, the roller configured to assist in placing and moving the inspection apparatus along the pipeline.

15. The method of claim 12, further comprising:
connecting a first extension arm to the first member and the carriage, the first extension arm configured to rotate the first member relative to the carriage, and
connecting a second extension arm to the second member and the carriage, the second extension arm configured to rotate the second member relative to the carriage.

16. The method of claim 15, wherein the first extension arm and the second extension arm comprise respective hydraulic cylinders.

17. The method of claim 16, further comprising connecting at least one hydraulic line between the ROV and the inspection apparatus, the at least one hydraulic line configured to extend and retract the respective hydraulic cylinders.

18. The method of claim 12, further comprising connecting at least one electrical line between the ROV and the inspection apparatus, the at least one electrical line configured to extend and retract the respective hydraulic cylinders.

19. The method of claim 13, wherein the inspection apparatus has a total of approximately four to approximately thirty-two PEC sensors.

20. The method of claim 13, wherein each of the first member and the second member has at least two and at most sixteen PEC sensors.

21. The method of claim 12, further comprising using the software component to calculate an average wall thickness of the section of the pipeline from the measurement signal.

22. The method of claim 21, further comprising taking a third round of measurements of the section of pipeline if the average wall thickness of the section of pipeline is below a desired amount, wherein the third round of measurements is taken using a fifth sensor.

23. The method of claim 22, wherein the fifth sensor is an ultrasonic sensor.

24. The method of claim 12, further comprising taking a third round of measurements after moving the inspection apparatus three inches down the pipeline.

25. The method of claim 12, further comprising taking a third round of measurements after moving the inspection apparatus five feet down the pipeline.

26. The method of claim 12, wherein the first sensor and the fourth sensor, the second sensor and the fourth sensor, and the first sensor and the third sensor alternate in taking rounds of measurements of the pipe to avoid magnetic interference.

27. A system for inspecting a submerged pipe, comprising:
a remotely operated vehicle (ROV); and
an inspection apparatus attached to the ROV, comprising:
a carriage; a first member having a first group of sensors including at least a first sensor and a second sensor configured to take a first round of measurements of a section of a pipe, the first member attached to a first side of the carriage;
a second member having a second group of sensors including at least a third sensor and a fourth sensor configured to take a second round of measurements of the section of the pipe, the second member attached to a second side of the carriage opposite the first side; and
a multiplexer device that receives a signal from at least the first sensor, second sensor, third sensor, and fourth sensor and generates a measurement signal using the signal from at least the first sensor, the second sensor, the third sensor, and the fourth sensor;
wherein adjacent all sensors alternate in taking rounds of measurements of the submerged pipe to avoid magnetic interference; and
wherein the carriage, the first member, and the second member are configured to surround a section of the pipe and are movably mountable on the pipe.

28. The system of claim 27, wherein the multiplexer device sends the measurement signal to a software component on the ROV, and wherein the software component determines, using the measurement signal, an average wall thickness of the section of pipe measured by the inspection apparatus.

29. The system of claim 27, wherein the at least first sensor, second sensor, third sensor, and fourth sensor comprise respective pulsed eddy current (PEC) sensors.

30. The system of claim 27, further comprising:
a first extension arm connected to the first member and the carriage, the first extension arm configured to rotate the first member relative to the carriage, and
a second extension arm connected to the second side member and the carriage, the second extension arm configured to rotate the second member relative to the carriage.

31. The system of claim 30, wherein the first extension arm and the second extension arm comprise respective hydraulic cylinders.

* * * * *